United States Patent [19]

Matsuura

[11] Patent Number: 4,886,510
[45] Date of Patent: Dec. 12, 1989

[54] URINE-COLLECTING DEVICE

[75] Inventor: Iwao Matsuura, Osaka, Japan

[73] Assignee: Nissho Corporation, Osaka, Japan

[21] Appl. No.: 298,309

[22] Filed: Jan. 18, 1989

Related U.S. Application Data

[60] Continuation of Ser. No. 96,440, Sep. 15, 1987, abandoned, which is a division of Ser. No. 10,664, Feb. 4, 1987, abandoned.

[30] Foreign Application Priority Data

Mar. 7, 1986 [JP] Japan .................................. 61-51098
Jul. 31, 1986 [JP] Japan ................................ 61-180993

[51] Int. Cl.[4] ............................................. A61F 5/44
[52] U.S. Cl. .................................. 604/353; 604/349; 604/351
[58] Field of Search ................. 604/317, 327, 332–353

[56] References Cited

U.S. PATENT DOCUMENTS

| | | | |
|---|---|---|---|
| 2,976,869 | 3/1961 | Silverstone et al. | 604/353 |
| 3,006,343 | 10/1961 | Baxter | 604/343 |
| 3,161,198 | 12/1964 | Moxley | 604/353 |
| 3,406,690 | 10/1968 | Igel et al. | 604/352 |
| 3,495,592 | 2/1970 | Herman | 604/338 |
| 3,841,332 | 10/1974 | Treacle | 604/335 |

FOREIGN PATENT DOCUMENTS

| | | | |
|---|---|---|---|
| 0078974 | 5/1983 | European Pat. Off. | 604/338 |
| 2242964 | 4/1975 | France | 604/351 |
| 1047947 | 11/1966 | United Kingdom | 604/347 |
| 1370622 | 10/1974 | United Kingdom | 604/344 |

Primary Examiner—Stephen C. Pellegrino
Attorney, Agent, or Firm—Armstrong, Nikaido Marmelstein, Kubovcik & Murray

[57] ABSTRACT

A urine-collecting device comprises a urine-collecting bag having an opening for inserting a penis therethrough, the opening being made on one side surface of the bag; a film for preventing a back flow of urine having a hole with a diameter being smaller than that of the opening; and a flexible sheet-like flange having a hole corresponding to the opening, wherein the film and flange are fixed to the bag in this order in a manner such that holes of the film and flange correspond to the opening of the bag, and a circumstance of the hole of the flange is only fixed to the bag.

Further, the film has a thin portion at the center and a thick portion therearound and the penis is softly sealed by the inner edge of the thin portion.

According to a device of the present invention, the device is applicable to any kind of patient, does not either cause a feeling of physical disorder or injure a penis, enables a bedridden old man or sick person to urinate while lying in order to contribute to the care thereof, and can be used sanitarily without causing a leak of urine.

8 Claims, 8 Drawing Sheets

FIG. 19
PRIOR ART

URINE-COLLECTING DEVICE

This application is a continuation of application Ser. No. 096,440 filed Sept. 15, 1987, now abandoned, which in turn is a division of application Ser. No. 010,664, filed Feb. 4, 1987, now abandoned.

BACKGROUND OF THE INVENTION

The present invention relates to a urine-collecting device, more particularly to a urine-collecting device used for old men or urinary incontinent men.

Hitherto, there have been often used urine-collecting devices at hospitals, and the like, which are put on to human bodies, in order to contribute to nursing of bedridden old men or urinary incontinent men. For example, there have been used such a condom-type device as disclosed in Japanese Examined Utility Model Publication No. 33367/1984; a funnel-type device as disclosed in Japanese Unexamined Utility Model Publication No. 113019/1985; a bag-like device as disclosed in Japanese Examined Utility Model Publication No. 49067/1980; a cylindrical device as disclosed in Japanese Unexamined Utility Model Publication No. 159422/1984, and the like.

Figures 15, 16:
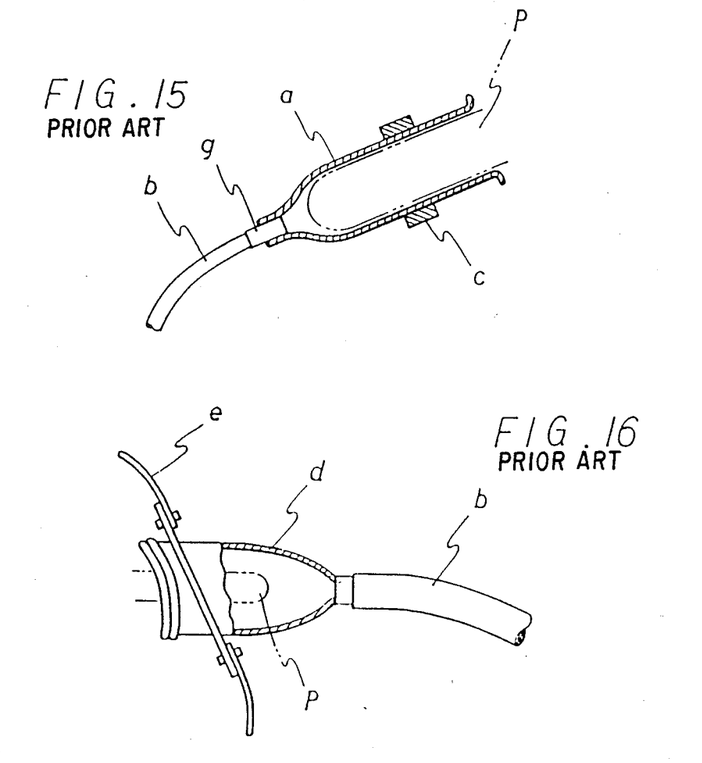
FIG. 15 is a sectional view of a conventional condom-type urine-collecting device.
FIG. 16 is a sectional view of a conventional funnel-type urine-collecting device.

The above-mentioned condom-type device comprises, as shown in FIG. 15, a condom-like rubber-made tube a, and a urine-introducing tube b is connected to a tip of the tube a. In using the device, a penis P is closely covered with the rubber-made tube a, and the tube a is fixed by means of a suitable belt c.

The above-mentioned funnel-type device comprises, as shown in FIG. 16, a funnel-like urine receiver d, and a urine-introducing tube b is connected to a tip of the receiver d. In using the device, the receiver b, whereinto a penis P is inserted, is fixed to the waist by means of a suitable band e.

Figure 17:
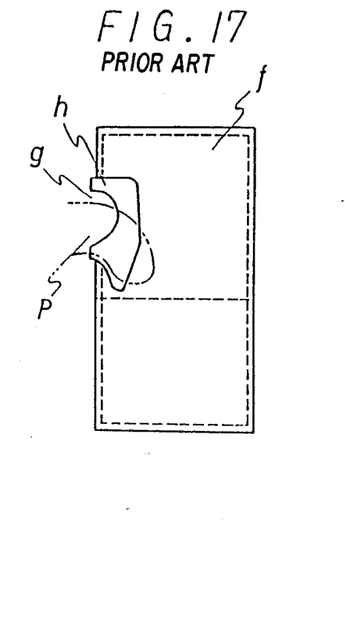
FIG. 17 is a side view of a conventional bag-like urine-collecting device.

The above-mentioned bag-like device comprises, as shown in FIG. 17, a flexible urine-collecting bag f having an opening g to let a penis insert into the bag f. After a penis P is iserted into the bag through the opening, the bag f is adhered to the body surface of a patient by means of an adhesive applied on fixing borders h which are attached to the bag f.

Figure 18:
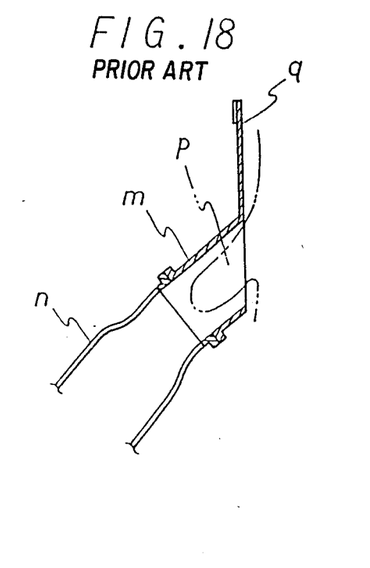
FIG. 18 is a sectional view of a conventional cylindrical urine-collecting device.

Further, the above-mentioned cylindrical device comprises, as shown in FIG. 18, a cylindrical part m having such an inside diameter that allows a penis to be inserted into the part m, a urine-collecting bag n which is attached to the part m by means of a ring, and an attaching member q integrally formed with the cylindrical part m. In such a device, a penis is inserted into the cylindrical part and then the device is fixed to the waist of a patient by means of a band, and the like which is attached to the attaching member q.

However, the above-mentioned conventional devices have the following problems. That is, in the condom-type device, there are problems that (1) the skin of a penis tends to fester by the use for many hours, because a penis is covered with the rubber-made tube a and thereby it cannot perform a cutaneous respiration, (2) the skin of a penis and blood vessels in a penis tend to be destroyed due to the fixation for many hours by a belt c, (3) the connection g with the introducing tube b is apt to be damaged due to the torsion thereof, when a patient with a device shifts sleeping positions, (4) not a few patients cannot use the devices since it is difficult to cover an unerected penis with the rubber-made tube a, and (5) a dipping method, which is a main method of producing the above condom-type devices, is hard to be mechanized, and, if the method is mechanized, it is difficult to reduce a production cost because it takes many hours to make the products.

The above-mentioned funnel-type devices have difference problems, though they almost solve the problems inherent in the condom-type devices, such that it highly costs to produce the funnel-type devices due to the poor mass-producibility (i.e. it takes many hours to produce the funnel-type devices), and the devices are inevitably apt to become dirty if they are used repeatedly.

In the above-mentioned bag-like devices, there are some problems that the application thereof is extremely limited because it is impossible, in case of an adult, to adhere the device to the human body because of the interruption by pubic hairs, and urine leaks out from a portion through which a penis is inserted in case of bedridden patients. The device has a sort of a function for preventing a back flow of urine, but it only functions during the use in a standing position.

Further, the above-mentioned cylindrical devices have a problem that a penis of an old man under medical care for a long time, which is frequently atrophied, is completely contained in the cylindrical part, and thereby urine is apt to leak out. This problem cannot be satisfactorily solved even if a valve for preventing a back flow is placed at an end portion of the cylindrical tube on the side of the introducing tube. For example, urine inevitably leaks out when the device is used under a condition wherein a penis faces upward (i.e. such a condition that a patient is lying on his back).

Figure 19:
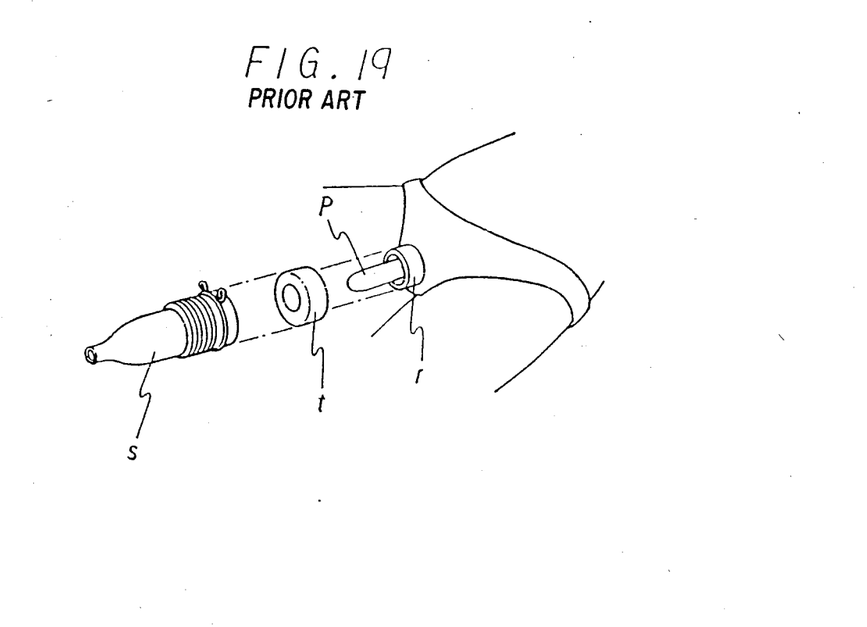
FIG. 19 is a perspective view of a funnel-type urine-collecting device which was previously proposed by the inventor and described in the specification of Japanese Utility Model Application No. 55282/1985.

In order to solve the above-mentioned various kinds of problems, the inventor previously proposed a funnel-type urine-collecting device (Japanese Utility Model Application No. 55282/1985). The device comprises, as shown in FIG. 19, a short cylindrical part r into which a penis P is inserted, a funnel-like urine-collecting piece s attached to the short cylindrical part r, and a thin film t for preventing a back flow of urine disposed between the short cylindrical part r and the funnel-like piece s. The device has advantages that it does not either injure a penis or allow urine to leak out, that is, it almost perfectly solves the drawbacks inherent in the above-mentioned condom-type, funnel-type, bag-like and cylindrical devices.

However, some patients have extremely atrophied penis (such a penis that is atrophied to as small as 1 cm), and to such patients there is a problem that even the above device cannot effectively function as a urine-collecting device.

An object of the present invention is to provide a urine-collecting device which can solve drawbacks inherent in the above-mentioned conventional devices. That is, an object of the present invention is to provide a first urine-collecting device which is applicable to any kind of patient, does not either cause a feeling of physical disorder during the use of the device or injure a penis, enables a bedridden old man or sick person to urinate while lying in order to contribute to the care thereof, and can be used sanitarily without causing the leak of urine.

Another object of the present invention is to provide a second urine-collecting device which can facilitate the attachment of a film for preventing a leak of urine.

SUMMARY OF THE INVENTION

In accordance with the present invention, there is provided a first urine-collecting device comprising a urine-collecting bag having an opening for inserting a penis therethrough, the opening being made on one side surface of the bag; a film for preventing a back flow of urine having a hole with a diameter being smaller than that of the opening; and a flexible sheet-like flange having a hole corresponding to the opening, chracterized in that the film and flange are fixed to the bag in this order in such a manner that holes of the film and flange correspond to the opening of the bag, and a circumstance of the hole of the flange is only fixed to the bag.

Further, in accordance with the present invention, there is also provided a second urine-collecting device comprising a urine-collecting bag having an opening for inserting a penis therethrough, the opening being made on one side surface of the bag, and a sheet-like flange formed integrally with the bag at a periphery of the opening; and a film for preventing a back flow of urine having a hole of which diameter is smaller than that of the opening, chracterized in that the film is formed to be cap-shaped and is attached to the flange to elastically cover the flange.

In the first urine-collecting device of the present invention, the device is firstly put on to a front attaching portion of an inner belt described hereinafter, by using a slit made in the front attaching portion, in such a manner that the front attaching portion is held between a flange and a urine-collecting bag. Thereafter, the front attaching portion is folded back toward a main body portion of the belt so as to let a penis be contained in the device through a hole of the film, and is fixed to the main body portion by means of a suitable fixing means. In that case, the fitting of the device to a penis is carried out easily and softly.

In receiving urine, a back flow of urine toward the human body is prevented by the film, though the urine from a penis sometimes transiently stays in the bag and splashes.

In the second urine-collecting device of the present invention, the attaching and detaching operation of the film can be easily performed since it only requires to cover the flange with the film. Accordingly, only a film can be exchanged with a new one whenever the film is used for several times, whereby the device can be always used in a sanitary condition.

DETAILED DESCRIPTION

Now, there is explained a urine-collecting device of the present invention, based on the accompanying drawings.

There is firstly explained an embodiment of a first urine-collecting device of the present invention.

Figure 1:
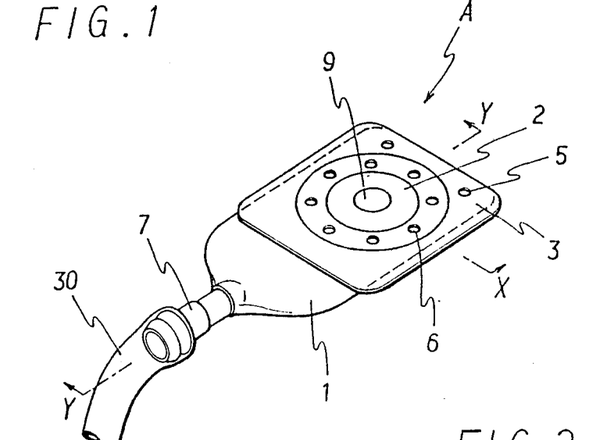
FIG. 1 is a perspective view of an embodiment of a first urine-collecting device of the present invention.

In FIG. 1, symbol a is a urine-collecting device composed of a urine-collecting bag 1, a film 2 for preventing a back flow of urine (hereinafter referred to as "preventing film") and a flange 3.

The urine-collecting bag 1 is such a portion that collects urine excreted from a penis. The bag 1 has, on one surface thereof, an opening 4 (shown in FIG. 4) to let a penis insert therethrough. One end of the bag 1 is narrowed in a funnel-like shape. The bag 1 is connected to a general urine-introducing tube 30 via a connecting part 7 attached to the above narrowed portion. A tip portion of the connecting part 7 is formed in an enlarged section, whereby the urine-collecting tube 30 connected thereto is not easily disconnected when the user rolls over in bed. On the other hand, a tip portion of the urine-introducing tube 30 might be formed in an enlarged section, and be inserted into the connecting part 7. That is, the shape of a tip portion of the connecting part 7 is not particularly limited. In short, any shape can be employed so long as the firm connection of the tube 30 can be obtained.

Figure 3:
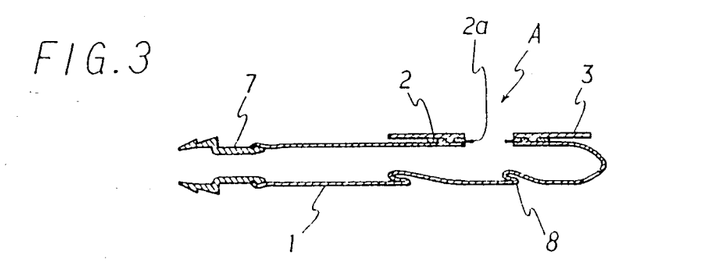
FIG. 3 is an end view taken along the line Y—Y of FIG. 1.

On a surface of the urine-collecting bag 1 contrary to the surface having an opening 4 (shown in FIG. 4), there are provided a suitable number of darts 8 (shown in FIG. 3) for expanding the bag 1 so as to insure the easy insertion of a penis in case of using the bag 1.

It is preferable that the urine-collecting bag 1 is made of a film-like or sheet-like soft synthetic resin material such as ethylene-vinylacetate copolymer (EVA), soft vinyl chloride resin (PVC) and polyethylene (PE). That is, the bag 1 is preferably made flexible, and transparent so as to contribute the nursing of a patient (i.e. to make sure the insertion of a penis).

Figure 2:
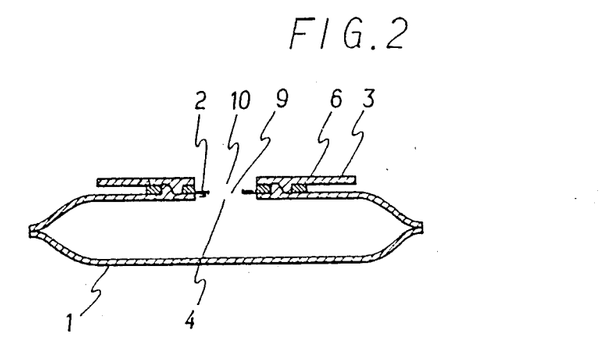
FIG. 2 is an enlarged end view taken along the line X—X of FIG. 1.
Figure 4:
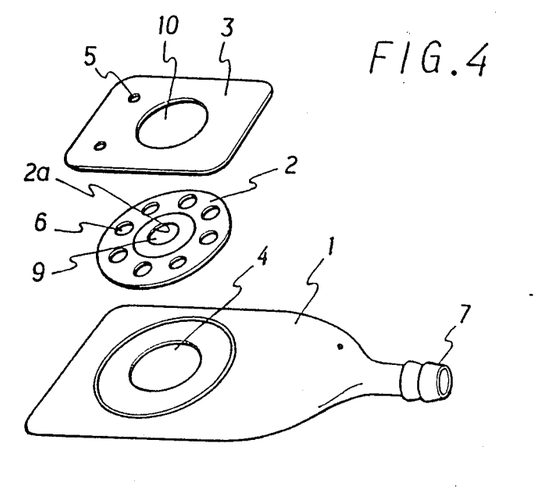
FIG. 4 is an exploded perspective view of the device shown in FIG. 1.

In the above preventing film 2, there are made, as shown in FIGS. 2 and 4, a central hole 9 to let a penis insert therethrough which hole having a diameter being smaller than that of the above-mentioned opening 4, and holes 6, at a peripheral portion of the film, for welding the flange 3 to the urine-collecting bag 1. The preventing film 2 consists of, as shown in FIG. 2, a thick portion and a thin portion. A portion to be fixed to the bag 1, that is, a portion outside of the opening 4 to let a penis insert therethrough is made thick and the other portion is made thin.

The preventing film 2 plays an important role to prevent a back flow of urine when excreting urine, and therefore preferably has a construction as described hereinafter according to the functions required therefor. The thick portion is required to have same degree of thickness for strength because there are made holes 6 for welding the flange 3 to the above-mentioned urine-collecting bag 1. For more detail, the film thickness of the thick portion is prefrably from 0.5 to 1.5 mm, more preferably about 1.0 mm. In contrast, the film thickness of the thin portion is preferably from 0.05 to 0.2 mm, more preferably from 0.05 to 0.1 mm so as to suitably stretch to allow a portion 2a (FIGS. 3 and 4) having a hole 9 defined therein to lightly fit a penis when inserting a penis into the hole 9, and have enough resistance to prevent a back flow of urine. As a material of the preventing film 2, it is desirable to employ a rubber-like elastic material such as natural rubber, isoprene rubber, urethane rubber and silicone rubber, because there are required of the material of the preventing film 2 that it can be made thin, and can suitably stretch to allow a portion 2a having a hole 9 defined therein to lightly fit a penis and softly contact with a penis when inserting a penis into the hole 9.

Though the thin portion around the inserting hole 9 is moderately elastic, the diameter of the hole 9 is preferably, for example, from 15 to 20 mm, more preferably about 18 mm in case of Japanese men in order to insure the easy insertion of penises of various kinds of sizes.

At a peripheral portion of the preventing film 2, there are made holes 6 for welding the flange 3 to the urine-collecting bag 1. Through the holes 6, the flange can be fixed to the urine-collecting bag 1. The number, shape and size of the holes 6 are not particularly limited, and can be suitably determined so long as the holes 6 enable the fixation of the flange 3 to the bag 1. The flange 3 might be, of course, directly welded to the bag 1 at the outside of the film 2 without using such holes as above-mentioned holes 6.

The preventing film 2 is fixed to the bag 1 by means of an adhesive, and the like as shown in FIG. 4. As an adhesive, it is desirable to use chloroprene, nitrile rubber, polyurethane and α-cyanoacrylate adhesives, and the like.

Figure 5:
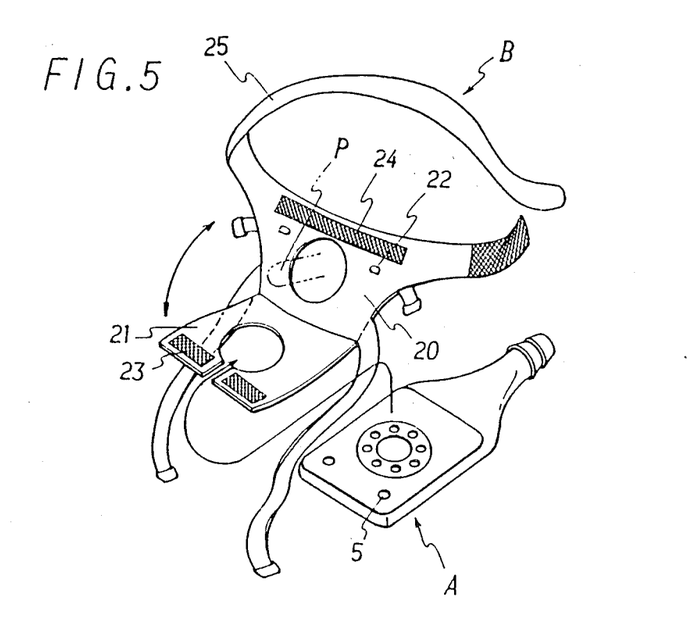
FIG. 5 is a view explaining a method of putting the device shown in FIG. 1 on to an inner belt of exclusive use.

The flange 3 is used as a connecting means when the devie A is put on to an inner belt (shown in FIG. 5). The flange 3 is sheet-like and has a hole 10 at its center. As a material of the flange 3, there can be employed, like the above-mentioned urine-collecting bag 1, soft synthetic resins such as soft vinyl chloride resin, ethylene-vinylacetate copolymer and polyethylene. The thickness of the flange 3 is preferably from 0.5 to 2 mm.

The flange 3 might be welded, as described above, to the bag 1 through holes 6 made on the preventing film 2, or directly welded to the bag 1 at the outside of the film 2 without using such holes 6. Of course, the flange 3 might be fixed to the bag 1 by means of an adhesive.

The device A of the present invention might be put on to the human body whenever a patient urinates. But, it is convenient to always put it on to the human body in case of bedridden old men or seriously ill person, because the unexpected urinary incontinence can be well treated thereby the service of a nurse can be saved.

Next, there is explained a method of putting on a device A of the present invention to an inner belt B. In FIG. 5, numeral 20 is a main body portion of the inner belt, numeral 21 is a front attaching portion, numeral 22 are projections to be engaged with fixing holes 5 made on the flange 3, numerals 23 and 24 are Velcro ® and numeral 25 is a band. In case of putting on the device A to the inner belt B, the device is firstly put on to a front attaching portion of the inner belt, by using a slit made in the attaching portion, in such a manner that the attaching portion is held between the flange 3 and the urine-collecting bag 1. Thereafter, the front attaching portion 21 is folded back toward a main body portion 20 of the inner belt so as to let a penis P be contained in the device through an inserting hole 9 of the preventing film 2. Then, the device A is fixed to the inner belt B by engaging the above Velcro ® 23 and 24 with each other and engaging the projections 22 with fixing holes 5.

In fixing the front attaching portion 21 to the main body portion 20 of the inner belt, any method can be employed so long as it is simple and sure. For example, hooks or buttons are employable.

The number of projections 22 might be determined in consideration of the sureness and simplicity of the connection. It is approximately 2 to 4. It is preferable that the shape of the projection 22 is somewhat clab-shaped so that the projections 22 do not easily come out of the fixing hole 5.

Further, the fixation of the flange 3 and the inner belt B can be performed by means of other methods such as hook and button, without using the above engagement of projections 22 with fixing holes 5.

Figure 6:
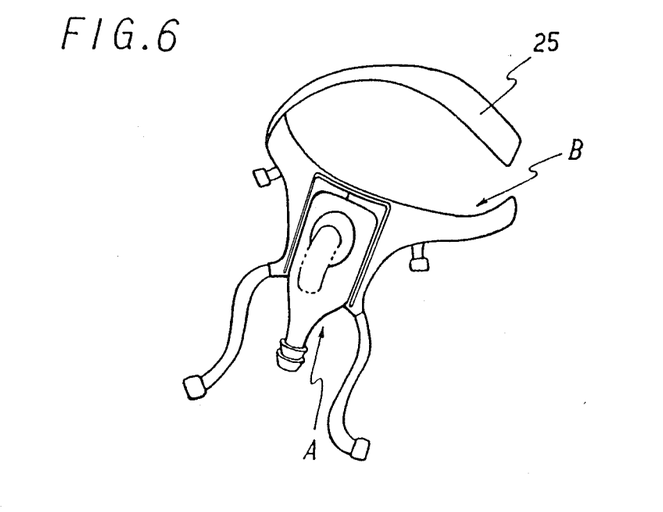
FIG. 6 is a view explaining a state wherein the first device is put on to the inner belt.

FIG. 6 is a view explaining a state wherein the device A is put on to the inner belt C according to the above-mentioned method. The device A is put on to the inner belt B in a manner such that a portion of the device A to be connected to a urine-introducing tube faces downward.

Next, there is explained an embodiment of a second urine-collecting device of the present invention.

Figure 7:
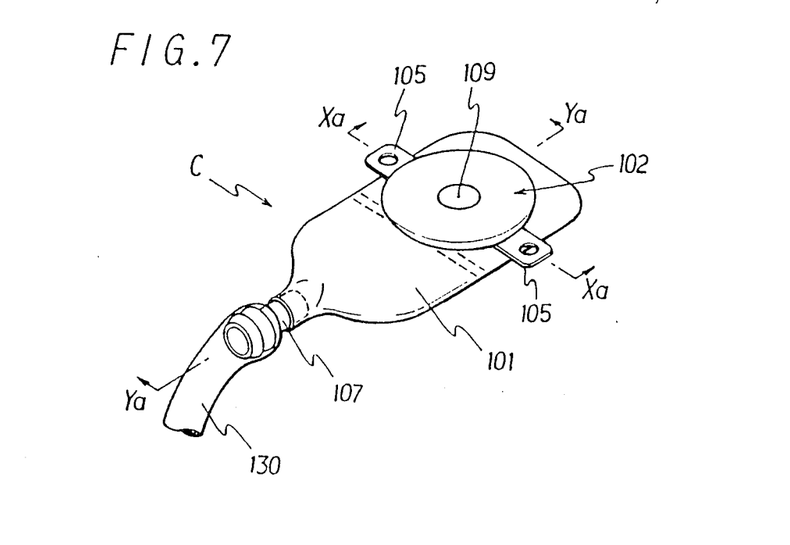
FIG. 7 is a perspective view of an embodiment of a second urine-collecting device of the present invention.
Figure 8:
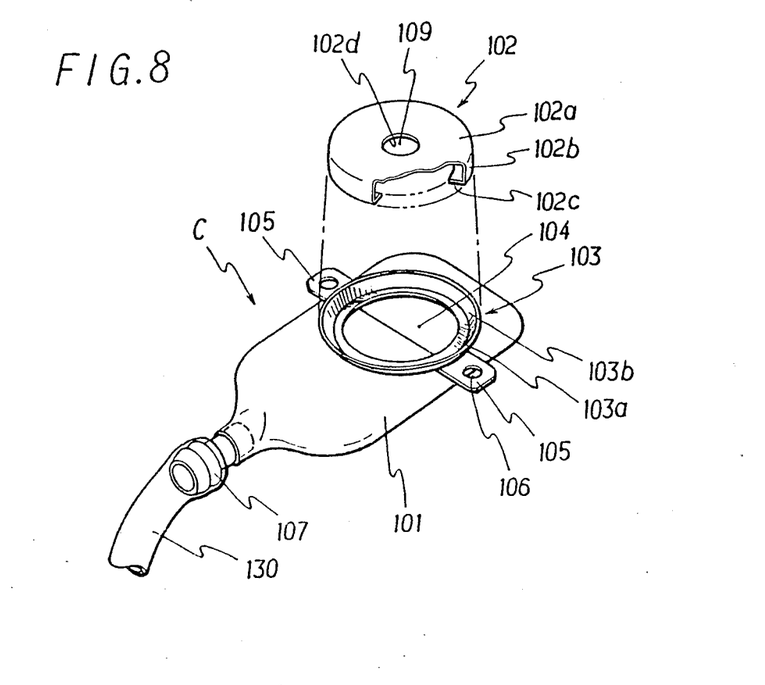
FIG. 8 is an exploded perspective view of the device shown in FIG. 7.
Figure 9:
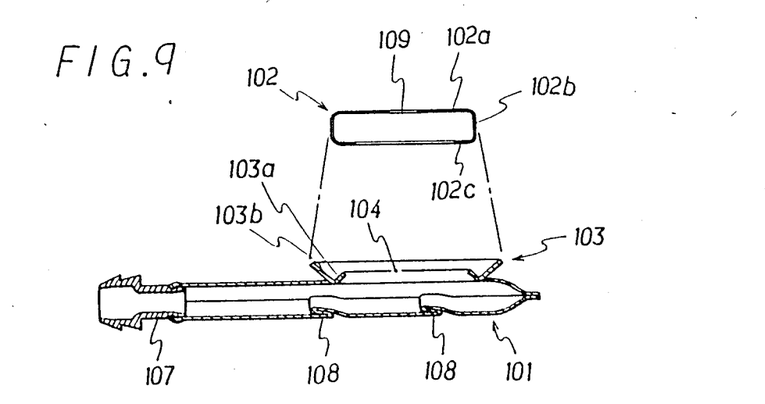
FIG. 9 is an enlarged sectional view taken along the line Ya—Ya of FIG. 7.
Figure 10:
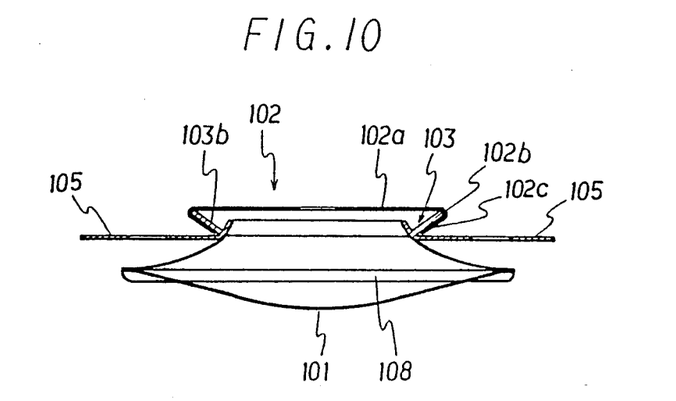
FIG. 10 is an enlarged end view taken along the line Xa—Xa of FIG. 7.
Figure 11:
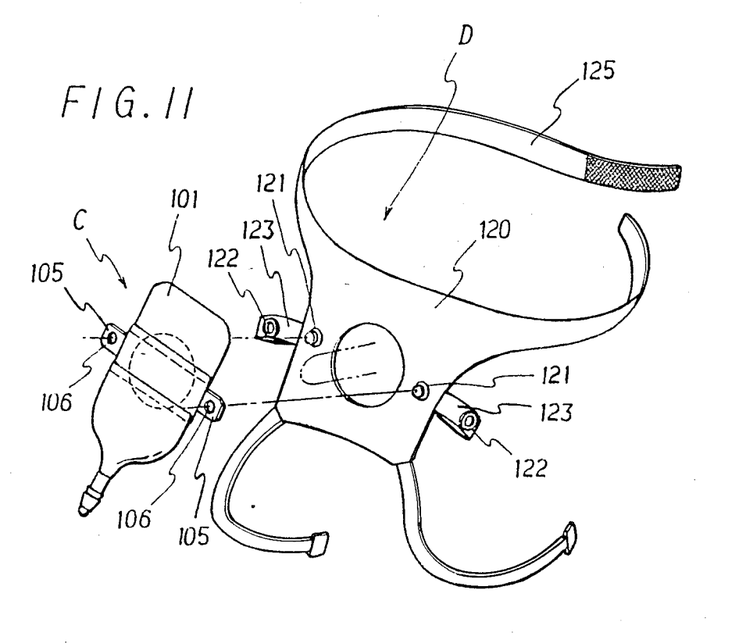
FIG. 11 is a view explaining a method of putting the device shown in FIG. 7 on to an inner belt of exclusive use.
Figure 12:
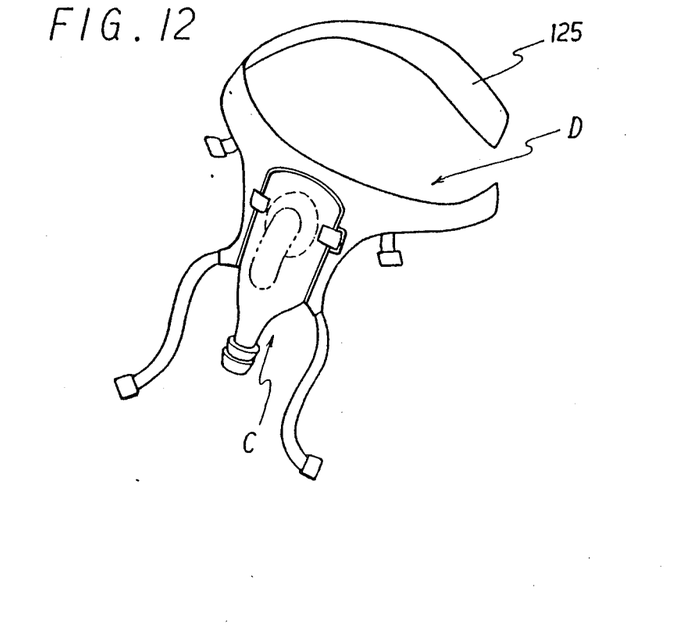
FIG. 12 is a view explaining a state wherein the device is put on to the inner belt.

FIG. 7 is a perspective view of an embodiment of a second urine-collecting device of the present invention;

FIG. 8 is an exploded perspective view of the device shown in FIG. 7;

FIG. 9 is an enlarged sectional view taken along the line Ya—Ya of FIG. 7;

FIG. 10 is an enlarged end view taken along the line Xa—Xa of FIG. 7;

FIG. 11 is a view explaining a method of putting on the device shown in FIG. 7 to an inner belt of exclusive use; and FIG. 12 is a view explaining a state wherein the second device is put on to the inner belt.

In FIGS. 7 and 8, symbol C is a urine-collecting device composed of a urine-collecting bag 101, a film 102 for preventing a back flow of urine (hereinafter referred to as "preventing film") and a flange 103.

The urine-collecting bag 101 is such a portion that collects urine excreted from a penis. The bag 101 has, on one side surface thereof, an opening 104 to let a penis insert therethrough. One end of the bag 101 is narrowed in a funnel-like shape. The bag 101 is connected to a general urine-introducing tube 130 via a connecting part 107 attached to the above narrowed portion. A tip portion of the connecting part 107 is formd in an enlarged section, whereby the urine-introducing tube 130 attached thereto is not easily disconnected due to rolling over in bed. On the other hand, a tip portion of the urine-introducing tube 130 might be formed in an enlarged section, and be inserted into the connecting part 107. That is, the shape of a tip portion of the connecting part 107 is not particularly limited. In short, any shape can be employed so long as the sure connection of the tube 130 can be obtained.

On a surface of the urine-collecting bag 101 opposite to the surface having an opening 104, there are provided a suitable number of darts 108 for expanding the bag 101 so as to insure the easy insertion of a penis in case of using the bag 101.

It is preferable that the urine-collecting bag 101 is made of a film-like or sheet-like soft synthetic resin material such as ethylene-vinylacetate copolymer (EVA), soft vinyl chloride resin (PVC) and polyethylene (PE). That is, the bag 101 is preferably made very flexible, and transparent so as to constibute to nursing of a patient (i.e. to make sure the insertion of a penis).

The above-mentioned flange 103 is integrally formed with the bag 101 at a periphery of the opening 104. The flange 103 is a ring-like part of which cross section is L-shaped, and consists of an inner flange 103a and an outer flange 103b. As a material of the flange 103, there can be employed, like the above-mentioned urine-collecting bag 1, soft synthetic resins such as soft vinyl chloride resin, ethylene-vinylacetate copolymer and polyethylene. The flange 103 is fixed to the bag 101 at a periphery of the opening 104 by a suitable method such as welding and adhesion. The role of the flange 103 is to hold a preventing film 102 (described hereinafter) in an elastically stretched condition. Therefore, the flange 103 is required to have hardness and to have enough flexibility to bend to a certain extent when covering the flange 103 with the preventing film 102 and taking the film 102 off. Owing to the flexibility, the attaching and detaching operations are facilitated. The thickness of the flange 103 is usually from about 0.5 to about 2 mm. It is preferable that the flange 103 has moderate hardness and flexibility.

The above-mentioned preventing film 102 is a cap-like part having a C-shaped section as shown in FIG. 9, and consists of, as shown in FIG. 8, a disc-like front wall 102a, a rim portion 102b extending downward from the edge of the wall 102a and a rear fringe portion 102c extending inwardly a little from the rim portion 102b. On the central portion of the front wall 102a, there is made an inserting hole 109 to let a penis insert therethrough which hole having a diameter being smaller than that of the opening 104. The inside diameter of the rim portion 102b is a little smaller than the outside diameter of the flange 103.

The front wall 102a of the preventing film 102 serves to prevent a back flow of excreted urine, while the rim portion 102b and rear fringe portion 102c serve to attach the film 102 to the flange 103. Therefore, the front wall 102a is required to be able to stop a back flow or scattering of urine, and to moderately stretch so as to allow a portion 102d (FIG. 8) having a hole 109 defined therein to lightly fit a penis and to softly contact with a penis. On the contrary, the rim portion 102b and rear fringe portion 102c are required to have such a strength that enables the tight connection between the preventing film 102 and flange 103. So, as a material of the preventing film 102, it is desirable to employ a rubber-like elastic material having large impact resilience such as natural rubber, isoprene rubber, urethane rubber and silicone rubber, because there are required of the material of the preventing film 102 that it can be made thin and has wholly sufficient elasticity.

In case of attaching the preventing film 102 to the urine-collecting bag 101, it is desirable to put the film 102 on the bag 101 in a manner such that the rim portion 102b and rear fringe portion 102c of the film 102 are closely contact with an outer surface of the outer flange 103b of the flange 103. In that case, the preventing film 102 stretches due to the elasticity thereof, closely contact with the flange 103 and is tightly held so as not to easily detach.

As is described hereinbefore, the front wall 102a of the preventing film 102 serves to prevent a back flow of excreted urine, while the rim portion 102b and rear fringe portion 102c serve to attach the film 102 to the flange 103, that is, to serve a holding function. Therefore, the front wall 102a is required to have a flexibility in particular, while the rim portion 102b and rear fringe portion 102c are required to have a strength to a certain extent. For more details, the film thickness of the front wall 102a is preferably from 0.05 to 0.2 mm, more preferably from 0.05 to 0.1 mm. In that case, the front wall 102a can suitably stretch to allow a portion 102d having a hole 109 defined therein to lightly fit a penis, and nevertheless have enough resistance to prevent a back flow of urine. Further, the film thickness of the rim portion 102b and rear fringe portion 102c is preferably from 0.5 to 1.5 mm, more preferably about 1 mm.

Though the front wall 102 around hole 109 is moderately elastic, the diameter of the hole 109 is preferably, for example, from 15 to 21 mm, more preferably about 18 mm in case of Japanese men in order to insure the easy insertion of penises of various kinds of sizes.

The urine-collecting bag 101 has, as shown in FIG. 8, projections 105 having button holes 106, on both sides of the opening 104. By using the projections 105, the attachment of the bag 101 to an inner belt D described hereinafter is carried out.

The device C of the present invention might be put on to the human body, whenever a patient urinates. But, it is convenient to always put it on to the human body in case of bedridden old men or serious ill cases, because the unexpected urinary incontinence can be well treated thereby the services of a nurse can be saved.

Next, there is explained a method of putting on a device C of the present invention to an inner belt D, based on FIG. 11. In FIG. 11, numeral 120 is a main body portion of the inner belt, numeral 121 are male buttons, numeral 122 are female buttons, and numeral 123 are cords. In case of putting on the device C to the inner belt D, the device is firstly applied to the main body portion 120 to let the male buttons 121 go through the button holes 106. Next, the male buttons 121 are put on the female buttons 122 and whereby the projections 105 of the device C is covered with the cords 123 to complete the putting on of the device C to the inner belt D.

In case of taking the device C off of the inner belt D, the operation opposite to that described hereinbefore might be carried out. In fixing the device C to the inner belt D, hooks or Velcro ® can also be employed besides the above buttons. That is, any method can be employed so long as the fixation is sure, and the attaching and detaching operation can be easily carried out.

FIG. 12 is a view explaining a state wherein the device C is put on to the inner belt D according to the above-mentioned method. The device C is put on to the inner belt D in a manner such that a portion of the device C to be connected to a urine-introducing tube faces downward.

Figure 13:
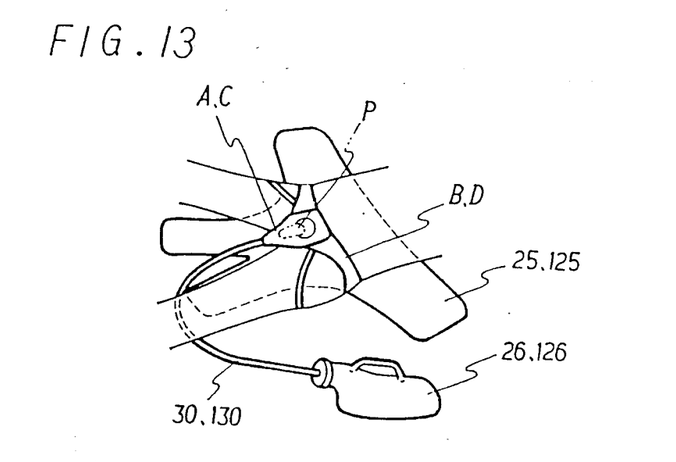
FIG. 13 is a view explaining a state wherein the first or second device of the present invention and a diaper cover of exclusive use are put on to a patient in a lying position.
Figure 14:
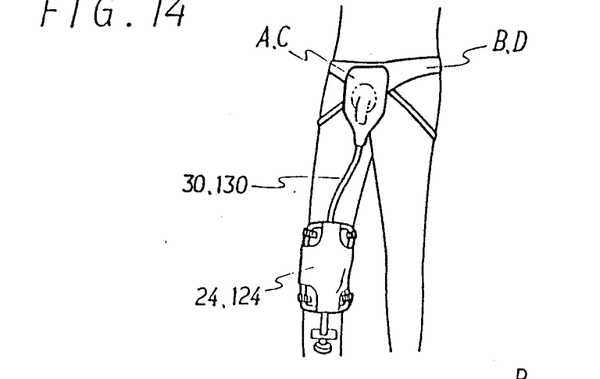
FIG. 14 is a view explaining a state wherein the first or second device of the present invention is put on to a patient in a standing position.

Next, there is explained how to actually use a first or second urine-collecting device of the present invention, based on FIGS. 13 and 14. When a patient lying on a bed uses the device, the device A, C which is put on to the human body of the patient by means of the inner belt B, D is connected, as shown in FIG. 13, to a urine-collecting bottle 26, 126 on the floor via a urine-introducing tube 30, 130. When the patient begins to urinate under this condition, the excreted urine is collected in the urine-collecting bag 1, 101 and then discharged into the urine-collecting bottle 26, 126 through the urine-introducing tube 30, 130. At that time, the urine excreted from a penis sometimes transiently stays in the bag and splashes, but a back flow of urine toward the human body is prevented by the film 2, 102, thereby urine can be perfectly collected without leaking out.

In FIG. 13, numeral 25, 125 is a diaper cover for collecting feces which is convenient for nursing of patients, because urine and feces can be separately collected by using the diaper cover together with the device A, C of the present invention. Due to the use of the diaper cover, there can be greatly reduced a nursing time and cost.

Since the discharging route of urine in the first or second device of the present invention is almost tightly-closed, the device can be used in almost any position (i.e. in a standing position, lying position, and the like). For example, a man in walker or in a wheelchair can also satisfactorily use the device. In that case, as shown in FIG. 14, the unexpected urinary incontinence can be well dealt with by fixing a urine-containing bag 24, 124 to a leg, and the like as shown in FIG. 14 and connecting the device to the urine-containing bag by means of a urine-introducing tube 30, 130.

The first or second device of the present invention is used in such a manner as described above. In particular, with respect to the second device, the film 102 is merely put on the flange. Therefore, the attaching and detaching operation of the film 102 is very easy. That is, the film 102 is simply put on the flange 103 by stretching the film 102 with fingers. After putting the film 102 on the flange 103, the film 102 closely contacts with the flange due to the elasticity of the film 102 itself. Further, the film 102 closely contacting with the flange 103 can be put off from the flange 103 by merely picking up the film 102.

Each time the device is used, the exchanging or sterilizing work of the film 102 becomes very easy, because the attaching and detaching operation of the film 102 is easy as described above. Further, it is possible to throw away the film after using it several times.

The urine-collecting device of the present invention having such a construction as described above has the following effects, when it is used as a urine-collecting device for a bedridden old man or urinary incontinent man.

(1) The urine-collecting device of the present invention can be effectively used to any kind of patient including a patient of which penis is extremely atrophied.

(2) The device does not either give a feeling of physical disorder to a patient or injure a penis, because it does not press a penis during the use thereof.

(3) The leak out of urine is almost perfectly prevented, since the discharging route of excreted urine is almost tightly-closed due to the function of a film for preventing a back flow of urine. Therefore, a patient in a lying position can use the device without soiling the body of a patient. Thus, the body of a patient can be always kept in a sanitary condition.

(4) The device can be applied to an unerected penis because the device does not have such a portion that strongly closely contacts with a penis. So, the device can be applied to a patient to which conventional urine-collecting devices are difficult to be applied.

(5) A patient in a standing position or in a wheelchair can comfortably use the device because the device can be used in almost any position. Further, it does not take much time and labor to use the device since it can be always put on to the human body. Therefore, it is very convenient to use the device for both a user and a nurse.

(6) Because the preventing film is integrally formed with the urine-collecting bag (in case of a first device of the present invention), there can be removed a trouble of putting on the film each time the device is used, whereby the time and labor of a nurse can be saved.

(7) It is not necessary to take off an inner belt which fixes the device to the human body, in case of fitting the device to a penis.

(8) The production cost can be reduced, because the urine-collecting bag comprises a simple bag and, therefore the device can be massproduced. Further, due to the cost reduction of the device, it is possible to provide an economical and disposable urine-collecting device. Thus, urine can be collected always in a sanitary condition.

(9) Further, in case of a second urine-collecting device of the present invention, the attaching and detaching operation of the preventing film is very easy, thereby it is not troublesome on attaching and detaching the film. Accordingly, the device can be used always in a sanitary condition by frequently exchanging the preventing films.

What I claim is:

1. A urine-collecting device comprising:
   a relatively flat urine collecting bag having front and back sides, said front side being provided with a first relatively large round opening;
   a flat film having a flexible thin portion and a thick portion around said flexible thin portion, said flexible thin portion having a diameter substantially equivalent to said first large round opening of said front side and having a thickness from 0.05 mm to about 0.2 mm, and said thick portion having a thickness from 0.5 mm to about 1.5 mm, said flexible thin portion being provided with a small hole at a center thereof, said small hole having a radially expandable contacting edge at an inner peripheral edge thereof through which a penis is to be inserted and having a diameter such that when the penis is inserted said radially expandable contacting edge expands to sealingly contact with a circumferential surface of the penis; and a flat flange provided with a second relatively large round opening having a diameter equivalent to said first large round opening of said front side, said flange being secured to said front side of said urine collecting bag holding said flat film therebetween by adhering said front side to said flange coaxially.

2. The urine-collecting device according to claim 1, wherein said diameter of said first small hole is from about 15 to about 20 mm.

3. The urine-collecting device according to claim 1 further comprising at least one dart at said back side.

4. The urine-collecting device according to claim 1 further comprising an outlet for feeding collected urine out therethrough.

5. The urine-collecting device according to claim 1, wherein said urine collecting bag is made of synthetic resin.

6. The urine-collecting device according to claim 1, wherein said flexible flat film is made of rubber.

7. The urine-collecting device according to claim 1, wherein said thick portion is provided with a plurality of small holes through which said front side is directly adhered to said flange.

8. The urine-collecting device according to claim 1, wherein said flange is provided with a plurality of holes.

* * * * *